US011490959B2

(12) United States Patent
Nau, Jr. et al.

(10) Patent No.: US 11,490,959 B2
(45) Date of Patent: Nov. 8, 2022

(54) SURGICAL INSTRUMENT FOR ENERGY-BASED TISSUE TREATMENT

(71) Applicant: COVIDIEN LP, Mansfield, MA (US)

(72) Inventors: William H. Nau, Jr., Longmont, CO (US); Arlen J. Reschke, Longmont, CO (US); Robert M. Sharp, Boulder, CO (US); Duane E. Kerr, Loveland, CO (US); James D. Allen, IV, Broomfield, CO (US)

(73) Assignee: COVIDIEN LP, Mansfield, MA (US)

( * ) Notice: Subject to any disclaimer, the term of this patent is extended or adjusted under 35 U.S.C. 154(b) by 655 days.

(21) Appl. No.: 16/523,178

(22) Filed: Jul. 26, 2019

(65) Prior Publication Data

US 2019/0343582 A1 Nov. 14, 2019

Related U.S. Application Data

(62) Division of application No. 13/933,683, filed on Jul. 2, 2013, now Pat. No. 10,368,945.
(Continued)

(51) Int. Cl.
*A61B 18/18* (2006.01)
*A61B 18/14* (2006.01)
(Continued)

(52) U.S. Cl.
CPC ...... *A61B 18/18* (2013.01); *A61B 17/320092* (2013.01); *A61B 18/1445* (2013.01);
(Continued)

(58) Field of Classification Search
CPC ............ A61B 18/18; A61B 17/320092; A61B 18/1445; A61B 2017/00398;
(Continued)

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 Y 9/2009
DE 2415263 A1 10/1975
(Continued)

OTHER PUBLICATIONS

Peterson et al. "Comparison of Healing Process Following Ligation with Sutures and Bipolar Vessel Sealing" Surgical Technology International (2001).
(Continued)

*Primary Examiner* — Tan-Uyen T Ho
*Assistant Examiner* — Rachel S Highland
(74) *Attorney, Agent, or Firm* — Carter, DeLuca & Farrell LLP

(57) ABSTRACT

A forceps includes a drive assembly and an end effector assembly having first and second jaw members movable between a spaced-apart position, a first approximated position, and a second approximated position. The drive assembly includes a drive housing and a drive bar. The proximal end of the drive bar is coupled to the drive housing, while the distal end of the drive bar is coupled to at least one of the jaw members. The drive housing and the drive bar are selectively movable in conjunction with one another between a first position and a second position to move the jaw members between the spaced-apart position and the first approximated position. The drive assembly is selectively activatable to move the drive bar independent of the drive housing from the second position to a third position to move the jaw members from the first approximated position to the second approximated position.

6 Claims, 9 Drawing Sheets

Related U.S. Application Data

(60) Provisional application No. 61/672,361, filed on Jul. 17, 2012.

(51) Int. Cl.
*A61B 17/32* (2006.01)
*A61B 17/00* (2006.01)
*A61B 17/29* (2006.01)
*A61B 18/00* (2006.01)

(52) U.S. Cl.
CPC .............. *A61B 2017/00398* (2013.01); *A61B 2017/00535* (2013.01); *A61B 2017/2902* (2013.01); *A61B 2017/2936* (2013.01); *A61B 2017/320093* (2017.08); *A61B 2017/320095* (2017.08); *A61B 2018/0063* (2013.01); *A61B 2018/00601* (2013.01); *A61B 2018/00607* (2013.01); *A61B 2018/1452* (2013.01)

(58) Field of Classification Search
CPC .. A61B 2017/00535; A61B 2017/2902; A61B 2017/2936; A61B 2017/320093; A61B 2017/320095; A61B 2018/00601; A61B 2018/00607; A61B 2018/0063; A61B 2018/1452
See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 4,848,338 A * | 7/1989 | De Satnick ............ A61B 17/29 606/171 |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| 5,817,119 A | 10/1998 | Klieman et al. |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| 6,221,069 B1 | 4/2001 | Daikuzono |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,491,202 B2 | 2/2009 | Odom et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,776,037 B2 | 8/2010 | Odom |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 8,343,150 B2 | 1/2013 | Artale |
| 8,382,754 B2 | 2/2013 | Odom et al. |
| 8,439,913 B2 | 5/2013 | Horner et al. |
| 8,679,140 B2 | 3/2014 | Butcher |
| RE44,834 E | 4/2014 | Dumbauld et al. |
| 8,968,311 B2 | 3/2015 | Allen, IV et al. |
| 2003/0114851 A1 | 6/2003 | Truckai et al. |
| 2006/0041254 A1 | 2/2006 | Francischelli et al. |
| 2006/0217697 A1 | 9/2006 | Lau et al. |
| 2007/0173814 A1 | 7/2007 | Hixson et al. |
| 2009/0093890 A1 | 4/2009 | Gelbart |
| 2009/0131934 A1 | 5/2009 | Odom et al. |
| 2009/0182327 A1 | 7/2009 | Unger |
| 2009/0204114 A1 | 8/2009 | Odom |
| 2010/0069953 A1* | 3/2010 | Cunningham ......... A61B 17/29 606/208 |
| 2010/0179539 A1* | 7/2010 | Nau, Jr. ............ A61B 18/1445 606/41 |
| 2010/0179547 A1 | 7/2010 | Cunningham et al. |
| 2011/0301604 A1 | 12/2011 | Horner et al. |
| 2011/0319886 A1 | 12/2011 | Chojin et al. |
| 2012/0022527 A1* | 1/2012 | Woodruff ........... A61B 18/1447 606/45 |
| 2012/0296324 A1 | 11/2012 | Chernov et al. |
| 2013/0150842 A1 | 6/2013 | Nau, Jr. et al. |
| 2013/0245623 A1 | 9/2013 | Twomey |
| 2013/0247343 A1 | 9/2013 | Horner et al. |
| 2013/0253489 A1 | 9/2013 | Nau, Jr. et al. |
| 2013/0255063 A1 | 10/2013 | Hart et al. |
| 2013/0267948 A1 | 10/2013 | Kerr et al. |
| 2013/0267949 A1 | 10/2013 | Kerr |
| 2013/0274736 A1 | 10/2013 | Garrison |
| 2013/0282010 A1 | 10/2013 | Mckenna et al. |
| 2013/0289561 A1 | 10/2013 | Waaler et al. |
| 2013/0296854 A1 | 11/2013 | Mueller |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0310832 A1 | 11/2013 | Kerr et al. |
| 2013/0325057 A1 | 12/2013 | Larson et al. |
| 2013/0331837 A1 | 12/2013 | Larson |
| 2013/0338666 A1 | 12/2013 | Bucciaglia et al. |
| 2013/0338693 A1 | 12/2013 | Kerr et al. |
| 2013/0345701 A1 | 12/2013 | Allen, IV et al. |
| 2013/0345706 A1 | 12/2013 | Garrison |
| 2013/0345735 A1 | 12/2013 | Mueller |
| 2014/0005663 A1 | 1/2014 | Heard et al. |
| 2014/0005666 A1 | 1/2014 | Moua et al. |
| 2014/0025052 A1 | 1/2014 | Nau, Jr. et al. |
| 2014/0025053 A1 | 1/2014 | Nau, Jr. et al. |
| 2014/0025059 A1 | 1/2014 | Kerr |
| 2014/0025060 A1 | 1/2014 | Kerr |
| 2014/0025066 A1 | 1/2014 | Kerr |
| 2014/0025067 A1 | 1/2014 | Kerr et al. |
| 2014/0025070 A1 | 1/2014 | Kerr et al. |
| 2014/0025073 A1 | 1/2014 | Twomey et al. |

(56) References Cited

U.S. PATENT DOCUMENTS

| | | |
|---|---|---|
| 2014/0031821 A1 | 1/2014 | Garrison |
| 2014/0031860 A1 | 1/2014 | Stoddard et al. |
| 2014/0046323 A1 | 2/2014 | Payne et al. |
| 2014/0066910 A1 | 3/2014 | Nau, Jr. |
| 2014/0066911 A1 | 3/2014 | Nau, Jr. |
| 2014/0074091 A1 | 3/2014 | Arya et al. |
| 2014/0100564 A1 | 4/2014 | Garrison |
| 2014/0100568 A1 | 4/2014 | Garrison |
| 2014/0121508 A1 | 5/2014 | Latimer et al. |
| 2014/0288541 A1 | 9/2014 | Eshkol et al. |

FOREIGN PATENT DOCUMENTS

| | | |
|---|---|---|
| DE | 02514501 A1 | 10/1976 |
| DE | 2627679 A1 | 1/1977 |
| DE | 03423356 A1 | 1/1986 |
| DE | 03612646 A1 | 4/1987 |
| DE | 3612646 A1 | 4/1987 |
| DE | 8712328 U1 | 2/1988 |
| DE | 8712328 U1 | 3/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| EP | 1707143 A1 | 10/2006 |
| EP | 1891891 A1 | 2/2008 |
| EP | 2353534 A1 | 8/2011 |
| JP | 61501068 | 9/1984 |
| JP | 61501068 A | 5/1986 |
| JP | 1024051 | 1/1989 |
| JP | 1147150 | 6/1989 |
| JP | 6502328 | 3/1992 |
| JP | 55106 | 1/1993 |
| JP | 0540112 A | 2/1993 |
| JP | H0540112 A | 2/1993 |
| JP | 6121797 | 5/1994 |
| JP | 6121797 A | 5/1994 |
| JP | 6285078 A | 10/1994 |
| JP | 06343644 | 12/1994 |
| JP | 6511401 | 12/1994 |
| JP | 6511401 A | 12/1994 |
| JP | H06343644 A | 12/1994 |
| JP | 07265328 | 10/1995 |
| JP | H07265328 A | 10/1995 |
| JP | 08056955 | 3/1996 |
| JP | 856955 | 5/1996 |
| JP | 08252263 A | 10/1996 |
| JP | 8289895 A | 11/1996 |
| JP | H08289895 | 11/1996 |
| JP | 8317934 A | 12/1996 |
| JP | 8317936 A | 12/1996 |
| JP | H08317934 | 12/1996 |
| JP | H08317936 | 12/1996 |
| JP | 910223 A | 1/1997 |
| JP | 09000538 A | 1/1997 |
| JP | H0910223 A | 1/1997 |
| JP | 9122138 A | 5/1997 |
| JP | 0010000195 A | 1/1998 |
| JP | H1024051 A | 1/1998 |
| JP | 10155798 A | 6/1998 |
| JP | H10155798 A | 6/1998 |
| JP | 1147149 | 2/1999 |
| JP | H1147150 A | 2/1999 |
| JP | 11070124 A | 3/1999 |
| JP | H1170124 A | 3/1999 |
| JP | 11169381 A | 6/1999 |
| JP | H11169381 | 6/1999 |
| JP | 11192238 A | 7/1999 |
| JP | H11192238 | 7/1999 |
| JP | 11244298 | 9/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001003400 A | 1/2001 |
| JP | 2001008944 | 1/2001 |
| JP | 2001029355 | 2/2001 |
| JP | 2001029356 | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2006015078 A | 1/2006 |
| JP | 2006501939 A | 1/2006 |
| JP | 2006095316 A | 4/2006 |
| JP | 2011125195 A | 6/2011 |
| JP | 0006030945 B2 | 11/2016 |
| JP | H0630945 B2 | 11/2016 |
| JP | 6502328 B2 | 4/2019 |
| SU | 401367 A1 | 10/1973 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |

OTHER PUBLICATIONS

"Electrosurgery: A Historical Overview" Innovations in Electrosurgery; Sales/Product Literature; Dec. 31, 2000. (6 pages).

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002.

Heniford et al. "Initial Results with an Electrothermal Bipolar Vessel Sealer" Surgical Endoscopy (2000) 15:799-801. (4 pages).

W. Scott Helton, "LigaSure Vessel Sealing System: Revolutionary Hemostasis Product for General Surgery"; Sales/Product Literature 1999.

(56) References Cited

OTHER PUBLICATIONS

Sigel et al. "The Mechanism of Blood Vessel Closure by High Frequency Electrocoagulation" Surgery Gynecology & Obstetrics, Oct. 1965 pp. 823-831.
Olsson et al. "Radical Cystectomy in Females" Current Surgical Techniques in Urology, vol. 14, Issue 3, 2001.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001 pp. 21-24.
Levy et al., "Update on Hysterectomy—New Technologies and Techniques" OBG Management, Feb. 2003.
Sengupta et al., "Use of a Computer-Controlled Bipolar Diathermy System in Radical Prostatectomies and Other Open Urological Surgery" ANZ Journal of Surgery (2001) 71.9 pp. 538-540.
Crawford et al. "Use of the LigaSure Vessel Sealing System in Urologic Cancer Surger" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
U.S. Appl. No. 14/019,094, filed Sep. 5, 2013, Garrison.
European Search Report EP 13176631 dated Oct. 28, 2013.
Michael Choti, "Abdominoperineal Resection with the LigaSure Vessel Sealing System and LigaSure Atlas 20 cm Open Instrument" Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
"Electrosurgery: A Historical Overview" Innovations in Electrosurgery; Sales-Product Literature; Dec. 31, 2000.
Johnson et al. "Evaluation of the LigaSure Vessel Sealing System in Hemorrhoidectormy" American College of Surgeons (ACS) Clinicla Congress Poster (2000).
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report" Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/Product Literature 2001.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Barbara Levy, "Use of a New Vessel Ligation Device During Vaginal Hysterectomy" FIGO 2000, Washington, D.C.
McLellan et al., "Vessel Sealing for Hemostasis During Pelvic Surgery" Int'l Federation of Gynecology and Obstetrics FIGO World Congress 2000, Washington, DC.
McLellan et al. "Vessel Sealing for Hemostasis During Gynecologic Surgery" Sales/Product Literature 1999.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric E. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/708,335, filed Dec. 7, 2012, Dumbauld.
U.S. Appl. No. 13/731,674, filed Dec. 31, 2012, Siebrecht.

(56) References Cited

OTHER PUBLICATIONS

U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/868,732, filed Apr. 23, 2013, Mueller.
U.S. Appl. No. 13/893,527, filed May 14, 2013, Horner.
U.S. Appl. No. 13/903,091, filed May 28, 2013, Nau.
U.S. Appl. No. 13/903,116, filed May 28, 2013, Nau.
U.S. Appl. No. 13/903,223, filed May 28, 2013, Payne.
U.S. Appl. No. 13/909,362, filed Jun. 4, 2013, Kerr.
U.S. Appl. No. 13/911,674, filed Jun. 6, 2013, Kerr.
U.S. Appl. No. 13/920,643, filed Jun. 18, 2013, Nau.
U.S. Appl. No. 13/922,377, filed Jun. 20, 2013, Allen.
U.S. Appl. No. 13/922,975, filed Jun. 20, 2013, McKenna.
U.S. Appl. No. 13/933,409, filed Jul. 2, 2013, Mueller.
U.S. Appl. No. 13/933,683, filed Jul. 2, 2013, Nau.
U.S. Appl. No. 13/936,510, filed Jul. 8, 2013, Kerr.
U.S. Appl. No. 13/947,991, filed Jul. 22, 2013, Kerr.
U.S. Appl. No. 13/969,204, filed Aug. 16, 2013, Bucciaglia.
U.S. Appl. No. 13/969,278, filed Aug. 16, 2013, Kerr.
U.S. Appl. No. 14/017,572, filed Sep. 4, 2013, Arya.
U.S. Appl. No. 14/019,031, filed Sep. 5, 2013, Garrison.

\* cited by examiner

SURGICAL INSTRUMENT FOR ENERGY-BASED TISSUE TREATMENT

CROSS REFERENCE TO RELATED APPLICATION

The present application is a divisional of U.S. patent application Ser. No. 13/933,683, filed on Jul. 2, 2013, which claims the benefit of and priority to U.S. Provisional Application Ser. No. 61/672,361, filed on Jul. 17, 2012, the entire contents of each of which are incorporated herein by reference.

BACKGROUND

Technical Field

The present disclosure relates to surgical instruments and, more particularly, to surgical instrument for treating tissue with energy.

Background of Related Art

A forceps is a plier-like instrument which relies on mechanical action between its jaws to grasp, clamp and constrict vessels or tissue. Energy-based forceps utilize both mechanical clamping action and energy, e.g., RF energy, ultrasonic energy, microwave energy, thermal energy, light energy, etc., to affect hemostasis by heating tissue and blood vessels to coagulate and/or cauterize tissue. Certain surgical procedures require more than simply cauterizing tissue and rely on the unique combination of clamping pressure, precise energy control and/or gap distance (i.e., distance between opposing jaw members when closed about tissue) to "seal" tissue, vessels, and certain vascular bundles. Typically, once a vessel is sealed, the surgeon has to accurately sever the vessel along the newly formed tissue seal. Accordingly, many forceps have been designed which incorporate a knife or blade member that effectively severs the tissue along the tissue seal. Alternatively, or additionally, energy may be utilized to facilitate tissue division.

SUMMARY

As used herein, the term "distal" refers to that portion that is further from an operator while the term "proximal" refers to that portion that is closer to an operator. As used herein, the term "treat" refers to performing a surgical treatment to tissue using energy, e.g. heating, sealing, or energized cutting of tissue. As used herein, the term "energy" refers broadly to include all types of energy used to treat tissue, e.g., RF energy, ultrasonic energy, microwave energy, thermal energy, light energy, etc. As used herein, the term "light energy source" refers broadly to include all types of devices that produce light for medical use (e.g., tissue treatment). These devices include lasers, light emitting diodes (LEDs), lamps, and other accessories that produce light anywhere along an appropriate electromagnetic spectrum (e.g., from infrared to ultraviolet).

Any or all of the aspects described herein, to the extent consistent with one another, may be used in conjunction with any of the other aspects described herein.

In accordance with one aspect of the present disclosure, a forceps is provided. The forceps generally includes an end effector assembly and a drive assembly. The end effector assembly includes first and second jaw members movable relative to one another between a spaced-apart position, a first approximated position, and a second approximated position. The drive assembly includes a drive housing and a drive bar. The proximal end of the drive bar is coupled to the drive housing, while the distal end of the drive bar is coupled to one or both of the jaw members. The drive housing and the drive bar are selectively movable, in conjunction with one another, between a first position and a second position to move the jaw members between the spaced-apart position and the first approximated position. The drive assembly is selectively activatable to move the drive bar independent of the drive housing from the second position to a third position to move the jaw members from the first approximated position to the second approximated position.

In one aspect, one or both of the jaw members is adapted to connect to a source of energy for treating tissue disposed between the jaw members.

In another aspect, a plunger is coupled to the drive housing and is selectively movable between a proximal position and a distal position for moving the jaw members between the spaced-apart position and the first approximated position. Alternatively, a handle is coupled to the drive housing and is selectively movable between an initial position and an actuated position for moving the jaw members between the spaced-apart position and the first approximated position.

In another aspect, the drive housing defines an internal chamber and the drive bar includes a proximal stop disposed at the proximal end thereof. The proximal stop is disposed within the internal chamber of the drive housing and is movable within the internal chamber upon activation of the drive assembly to move of the drive bar from the second position to the third position.

In yet another aspect, the drive housing further includes a spring disposed within the internal chamber of the drive housing. The spring is configured, upon activation of the drive assembly, to bias the drive bar distally relative to the drive housing to thereby move the drive bar from the second position to the third position.

In some aspects, the spring is initially encased in a thermally-activatable material disposed within the internal chamber to inhibit movement of the drive bar from the second position to the third position. One or more heaters may be coupled to the internal chamber and configured such that, upon activation of the drive assembly, the heaters melt the material to thereby permit movement of the drive bar from the second position to the third position under the bias of the spring.

In other aspects, the proximal stop divides the internal chamber into a proximal portion and a distal portion and includes a valve that is transitionable between a closed condition, inhibiting passage of fluid through the valve from the distal portion to the proximal portion, and an open condition, permitting passage of fluid through the valve from the distal portion to the proximal portion. The valve may initially be disposed in the closed condition such that the fluid substantially fills the proximal portion of the internal chamber, thus inhibiting movement of the drive bar from the second position to the third position. Upon activation of the drive assembly, the valve is transitioned to the open condition to permit fluid to flow therethrough to thereby permit movement of the drive bar from the second position to the third position under the bias of the spring.

In accordance with another aspect of the present disclosure, a forceps is provided. The forceps includes an end effector assembly and a drive assembly. The end effector assembly includes first and second jaw members movable relative to one another between a spaced-apart position, a first approximated position, and a second approximated position. The drive assembly includes a drive housing defining an internal chamber and a drive bar coupled to the end effector assembly at a distal end thereof and defining a proximal stop at the proximal end thereof. The proximal stop is slidably disposed within the internal chamber of the drive housing. The drive bar and drive housing are movable in conjunction with one another between a first position and a second position for moving the jaw members between the spaced-apart position and the first approximated position. A spring is disposed within the internal chamber of the drive housing and is configured to bias the drive bar distally relative to the drive housing. A thermally-activatable material is disposed within the internal chamber of the drive housing and encases the spring so as to inhibit the spring from biasing the drive bar distally relative to the drive housing. One or more heaters is thermally coupled to the internal chamber. The heater(s) is selectively activatable to melt the material to thereby permit the spring to bias the drive bar distally relative to the drive housing from the second position to a third position to move the jaw members from the first approximated position to the second approximated position.

In one aspect, one or both of the jaw members is adapted to connect to a source of energy for treating tissue disposed between the jaw members. The heater(s) may be adapted to connect to the source of energy for melting the material.

In another aspect, the heater(s) is configured to melt the material according to a pre-determined function such that the jaw members are moved between the first approximated position and the second approximated position in accordance with the pre-determined function.

In accordance with yet another aspect of the present disclosure, a forceps is provided. The forceps includes an end effector assembly and a drive assembly. The end effector assembly includes first and second jaw members movable relative to one another between a spaced-apart position, a first approximated, and a second approximated position. The drive assembly includes a drive housing defining an internal chamber and a drive bar coupled to the end effector assembly at a distal end thereof. A proximal end of the drive bar defines a proximal stop slidably disposed within the internal chamber of the drive housing. The drive bar and drive housing are movable in conjunction with one another between a first position and a second position for moving the jaw members between the spaced-apart position and the first approximated position. A spring is disposed within the internal chamber of the drive housing and is configured to bias the drive bar distally relative to the drive housing. A fluid substantially fills the proximal portion of the internal chamber defined between a distal end of the internal chamber and the proximal stop so as to inhibit the spring from biasing the drive bar distally relative to the drive housing. A valve is disposed within an aperture extending through the proximal stop and is transitionable between a closed condition inhibiting the spring from biasing the drive bar distally relative to the drive housing, and an open condition permitting fluid to pass through the valve from the proximal portion of the internal chamber to a distal portion of the internal chamber defined between the proximal stop and a proximal end of the internal chamber. In the open condition of the valve, the spring is permitted to bias the drive bar distally relative to the drive housing from the second position to a third position to move the jaw members from the first approximated position to the second approximated position.

In one aspect, one or both of the jaw members is adapted to connect to a source of energy for treating tissue disposed between the jaw members.

In another aspect, the valve is configured to transition between the closed condition and the open condition according to a first pre-determined function such that the jaw members are moved between the first approximated position and the second approximated position in accordance with the first pre-determined function. Additionally or alternatively, the fluid is configured to flow through the valve according to a second pre-determined function such that the jaw members are moved between the first approximated position and the second approximated position in accordance with the second pre-determined function.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
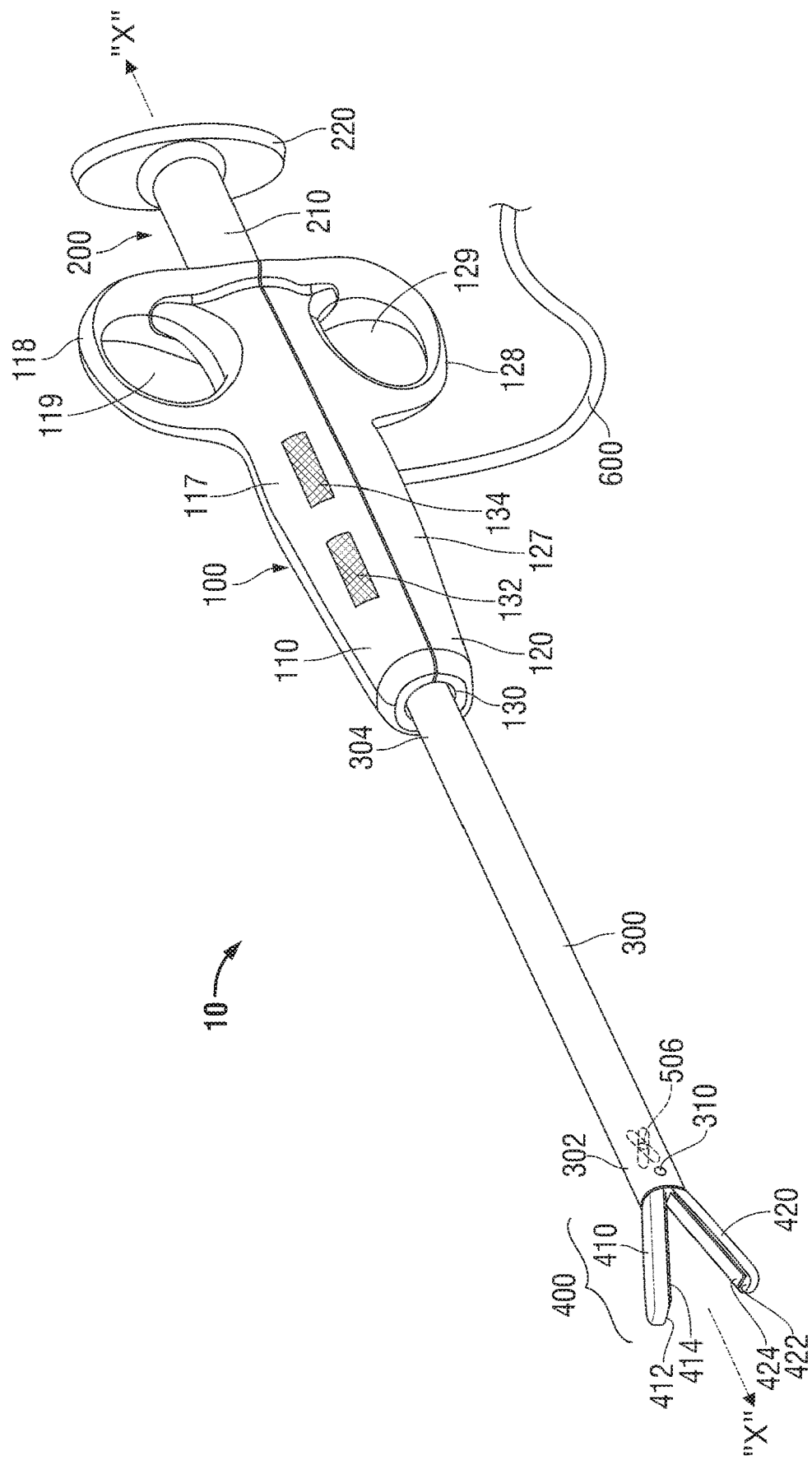
FIG. 1 is a front, perspective view of one embodiment of a surgical instrument provided in accordance with the present disclosure, wherein jaw members of the surgical instrument are shown disposed in a spaced-apart position.

The present disclosure relates generally to apparatus, systems and methods for treating tissue, e.g., heating, sealing, and/or dividing tissue using energy. The present disclosure is particularly advantageous for treating tissue using light energy, although the present disclosure is equally applicable for use with various other forms of energy, e.g., RF energy, ultrasonic energy, microwave energy, thermal energy, etc. However, while different considerations may apply depending on the particular form of energy used, the novel aspects of the present disclosure remain generally consistent regardless of the form of energy used. For simplicity and consistency purposes, the various aspects of the present disclosure will be described hereinbelow with respect to treating tissue using light energy.

Various drive assemblies and end effector assemblies configured for use with forceps 10 (FIG. 1), forceps 10' (FIGS. 8A-8B), or any other suitable surgical instrument, are described in detail hereinbelow with reference to FIGS. 1-9B. In particular, the drive assemblies and end effector assemblies described herein each include features that are configured to vary the pressure exerted on tissue disposed between the jaw members thereof while treating tissue in order to facilitate sealing and/or cutting of tissue. As will be described below, such a feature is particularly advantageous with respect to tissue treatment using light energy. However, the present disclosure is equally applicable for treating tissue using other forms of energy.

Light energy is suitable for sealing tissue since it is converted into heat energy by absorption at a molecular level. That is, light energy at optical wavelengths (e.g., from about 200 nm to about 11,000 nm) is used to heat tissue due to absorption of light energy at these wavelengths. However, optical properties of tissue are known to change during heating. For example, properties such as the absorption coefficient ($\mu_a$), scattering coefficient ($\mu_s$), and anisotropy coefficient (g) have been shown to change as a function of temperature and time. These properties, in turn, affect the transmission and reflection of light as it interacts with tissue.

It has been found that, due to the above, varying the pressure exerted on tissue during the application of light energy to tissue facilitates the formation of a tissue seal and/or the division of tissue along the tissue seal. More specifically, it has been found that initially applying a relatively smaller pressure to tissue allows for maximum absorption of light energy by tissue and that, once tissue has absorbed a sufficient amount of energy, i.e., once tissue has been sufficiently heated, increasing the pressure applied to tissue facilitates formation of the tissue seal. Further, it has also been found that increasing the pressure applied to tissue, e.g., after formation of a tissue seal, facilitates the cutting of tissue using light energy. The drive assemblies and end effector assemblies described hereinbelow implement these advantageous findings by providing features that are configured to vary the pressure exerted on tissue disposed between the jaw members thereof during the application of light energy to tissue in order to facilitate sealing and/or cutting of tissue.

Figure 2:
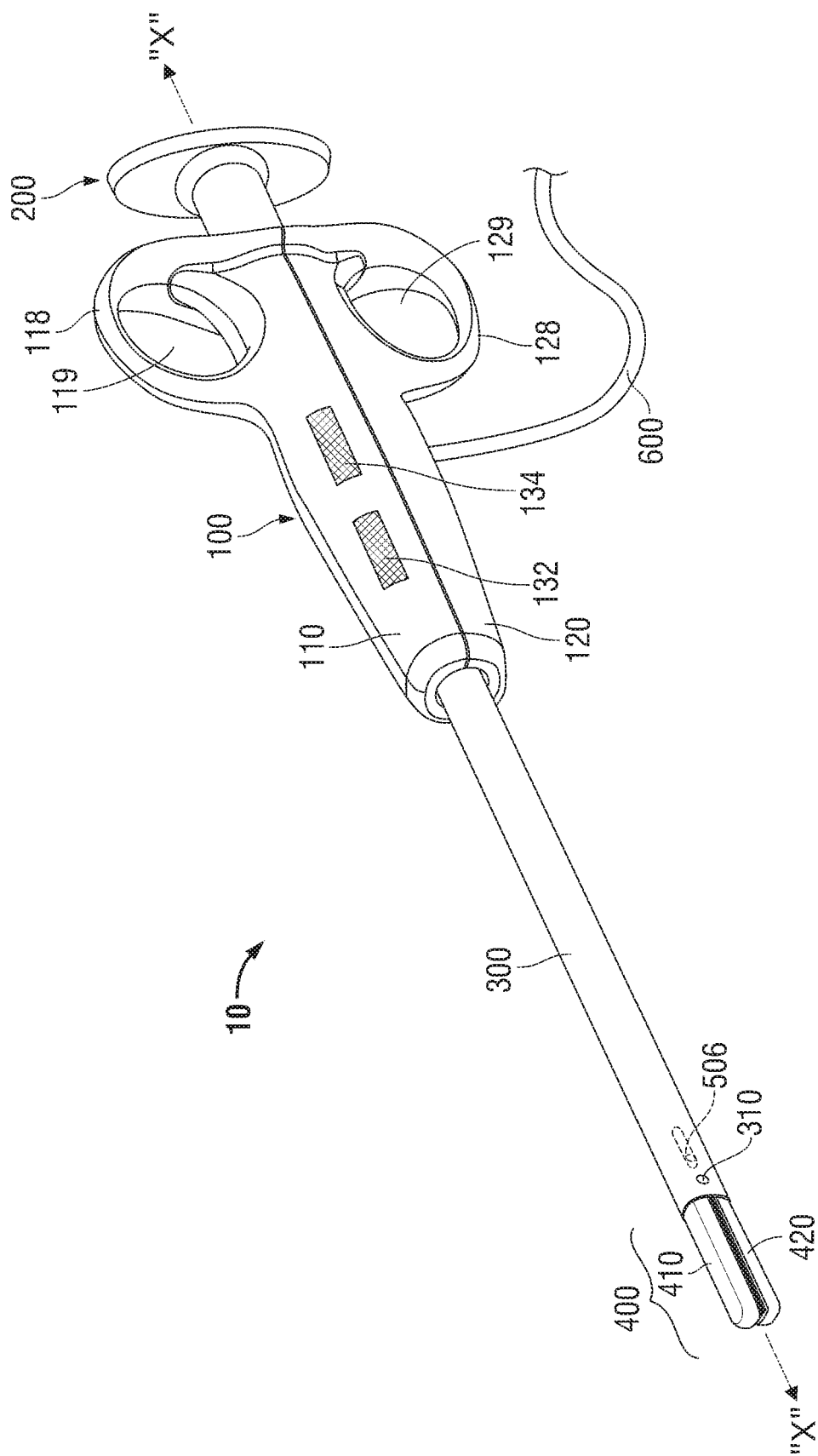
FIG. 2 is a front, perspective view of the surgical instrument of FIG. 1, wherein jaw members of the surgical instrument are shown disposed in an approximated position.
Figure 3:
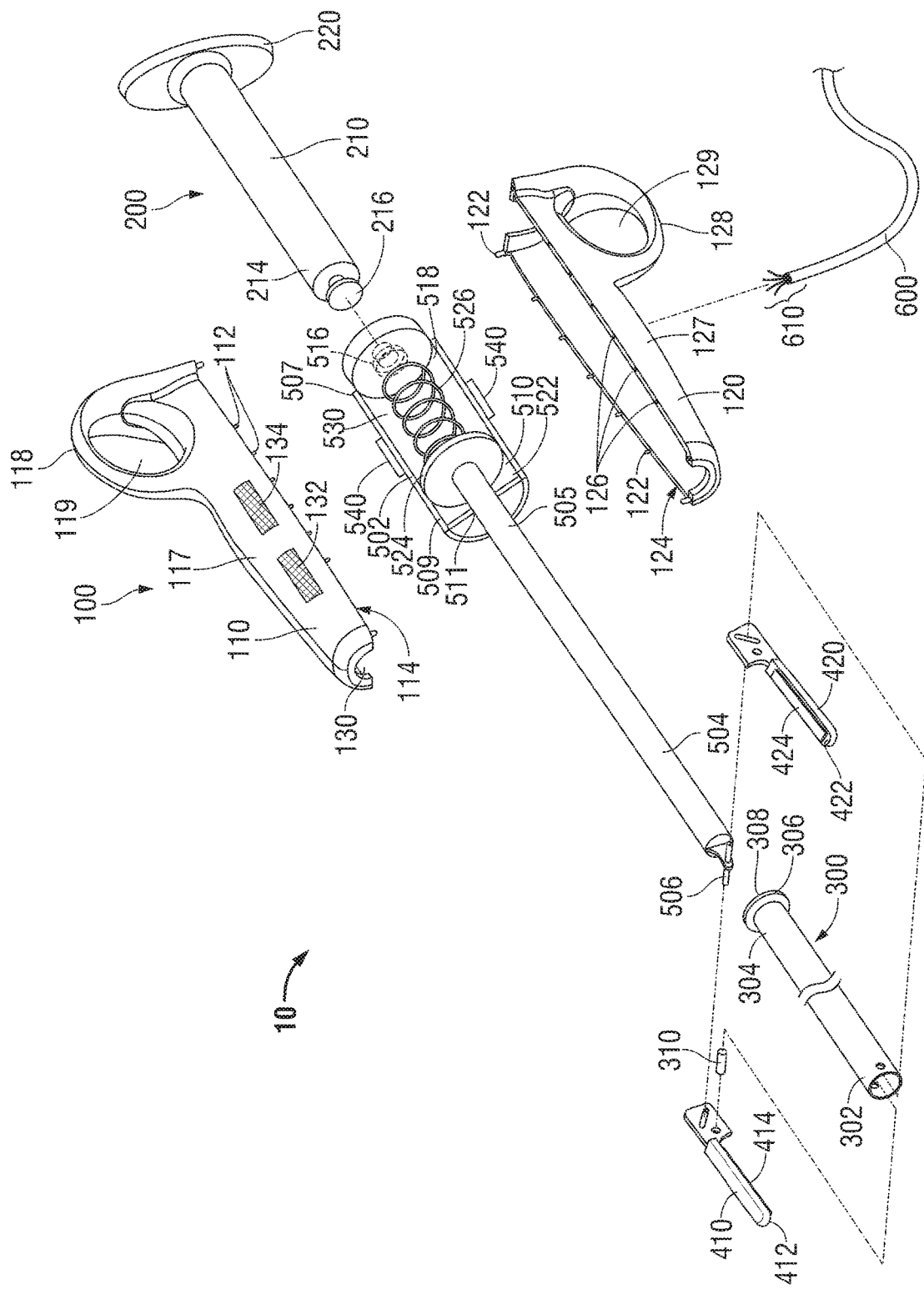
FIG. 3 is a side, perspective view of the surgical instrument of FIG. 1 shown with parts separated.

Referring now to FIGS. 1-3, a forceps is shown generally identified by reference numeral 10. Forceps 10 defines a longitudinal axis "X-X" and includes a handle assembly 100, a plunger 200 extending proximally from handle assembly 100, a shaft 300 extending distally from handle assembly 100, an end effector assembly 400 disposed at distal end 302 of shaft 300, and a drive assembly 500 (FIGS. 4A, 5A, and 6A) operably coupled to plunger 200 and end effector assembly 400. End effector assembly 400 includes a pair of opposed jaw members 410, 420 movable relative to one another between a spaced-apart position (FIG. 1) and one or more approximated positions (FIG. 2) for grasping tissue therebetween. Plunger 200 is selectively translatable relative to handle assembly 100 between an extended or proximal position (FIG. 1), wherein plunger 200 substantially extends proximally from handle assembly 100, and an inserted or distal position (FIG. 2), wherein plunger 200 is substantially disposed within handle assembly 100. More specifically, as will be described in greater detail below, plunger 200 and drive assembly 500 (FIGS. 4A, 5A, and 6A) cooperate with one another to effect movement of jaw members 410, 420 relative to one another between the spaced-apart position (FIG. 1) and one or more approximated positions (FIG. 2) upon movement of plunger 200 between the proximal position (FIG. 1) and the distal position (FIG. 2).

Forceps 10 further includes a cable 600 extending from handle assembly 100. Cable 600 includes a plurality of wires 610 extending therethrough that separate within handle assembly 100 to provide energy to handle assembly 100 and/or to extend through shaft 300 to provide energy, e.g., light energy, to end effector assembly 400, as will be described in greater detail below. Cable 600 is adapted to connect to a generator (not shown) or other suitable power source, although forceps 10 may alternatively be configured as a battery powered instrument (see FIGS. 8A-8B).

With continued reference to FIGS. 1-3, handle assembly 100 is formed from first and second housing parts 110, 120 that are engagable with one another to form handle assembly 100. More specifically, each housing part 110, 120 includes a plurality of posts 112, 122 disposed on engaging surfaces 114, 124, respectively, thereof and extending therefrom. Housing part 110 includes a plurality of apertures (not shown) defined within engaging surface 114 thereof, and housing part 120 similarly includes a plurality of apertures 126 defined within engaging surface 124 thereof. Posts 112 of housing part 110 are positioned to oppose apertures 126 of housing part 120 and, similarly, posts 122 of housing part 120 are positioned to oppose the apertures (not shown) of housing part 110 such that, upon approximation of housing parts 110, 120, posts 112 are engaged within apertures 126 and posts 122 are engaged within different apertures (not shown) defined within housing part 110 to engage first and second housing parts 110, 120, respectively, to one another.

Each housing part 110, 120 further includes an elongated body portion 117, 127 and an ergonomically-configured handle 118, 128 extending outwardly therefrom. Each handle 118, 128 defines a finger hole 119, 129 therethrough for receiving a finger of the user. As can be appreciated, finger holes 119, 129 facilitate grasping of handle assembly 100 during translation of plunger 200 relative to handle assembly 100 between the proximal and distal positions to transition jaw members 410, 420 of end effector assembly 400 between the spaced-apart and approximated positions.

Continuing with reference to FIGS. 1-3, and to FIG. 3 in particular, body portions 117, 127 of housing parts 110, 120, respectively, cooperate with one another to define a longitudinally-extending lumen 130 therethrough. Lumen 130 is disposed about longitudinal axis "X-X" and is configured to house drive assembly 500 and at least a portion of plunger 200 therein. More specifically, lumen 130 is configured to permit reciprocation of drive assembly 500 and plunger 200 at least partially therethrough to transition jaw members 410, 420 between the more spaced-apart position and the one or more approximated positions. One or both of housing parts 110, 120 may further include one or more switch assemblies, e.g., first and second switch assemblies 132, 134, respectively, that are ergonomically disposed on handle assembly 100 and are coupled to cable 600 for selectively controlling the supply of energy to jaw members 410, 420, and/or for selectively activating other components of forceps 10, e.g., heaters 540 of drive assembly 500 (as will be described in greater detail below (see FIGS. 4A, 5A, and 6A).

Plunger 200 generally includes a rod 210 and a knob 220 disposed at a proximal end of rod 210. Rod 210 further defines an engagement feature 216 at distal end 214 thereof that is configured to engage plunger 200 and drive assembly 500 to one another, as will be described in greater detail below. Knob 220 is configured for single handed-used, e.g., where knob 220 is grasped, or palmed by the user, while the user grasps handle assembly 100 by engagement of the user's fingers within finger holes 119, 129 of handles 118, 128, respectively, to facilitate translation of plunger 200 relative to handle assembly 100, e.g., between the proximal position (FIG. 1) and the distal position (FIG. 2), although other grasping configurations, e.g., two-handed operation, are also contemplated.

Continuing with reference to FIG. 3, shaft 300 is coupled to handle assembly 100 at proximal end 304 thereof and operably engages jaw members 410, 420 of end effector assembly 400 at distal end 302 thereof. More specifically, shaft 300 extends into lumen 130 of handle assembly 100 formed via the engagement of first and second housing parts 110, 120, respectively, and includes an annular flange 306 disposed at proximal end 304 thereof that is received within annular slot 136 (FIG. 4A) defined within handle assembly 100 and disposed about lumen 130. The engagement of annular flange 306 within annular slot 136 (FIG. 4A), upon engagement of first and second housing parts 110, 120 to one another, secures proximal end 304 of shaft 300 and handle assembly 100 to one another.

Shaft 300 further includes a lumen 308 extending longitudinally therethrough from proximal end 304 to distal end 302 thereof. A pivot pin 310 extends transversely through lumen 308 of shaft 300 towards distal end 302 of shaft 300. Pivot pin 310 is configured to rotatably support first and second jaw members 410, 420 of end effector assembly 400 at distal end 302 of shaft 300. However, although end effector assembly 400 is shown as a bilateral assembly, i.e., wherein both jaw members 410, 420 are movable relative to one another and with respect to shaft 300, end effector assembly 400 may alternatively be configured as a unilateral assembly, i.e., wherein one of the jaw members, e.g., jaw member 420, is fixed relative to shaft 300, while the other jaw member, e.g., jaw member 410, is movable about pivot 310 relative to both jaw member 420 and shaft 300. Lumen 308 may further be configured to route one or more wires 610a from cable 600 to end effector assembly 400 for selectively energizing jaw member 410 and/or jaw member 420 of end effector assembly 400.

With continued reference to FIG. 3, drive assembly 500 generally includes a drive housing 502 and a drive bar 504 coupled to and extending distally from drive housing 502. Drive housing 502 is slidably positioned within lumen 130 of handle assembly 100, while drive bar 504 extends distally from drive housing 502 and though shaft 300, ultimately engaging jaw members 410, 420 via cam pin 506. As such, longitudinal translation of drive bar 504 relative to end effector assembly 400 pivots jaw members 410, 420 relative to one another between the spaced-apart position (FIG. 4B) and one or more approximated positions, e.g., a first approximated position (FIG. 5B) and a second approximated position (FIG. 6B). More specifically, drive bar 504 is longitudinally translatable, in conjunction with plunger 200 and drive housing 502, between a first position, corresponding to the spaced-apart position of jaw members 410, 420 (FIG. 4B), and a second position, corresponding to the first approximated position of jaw members 410, 420 (FIG. 5B). Drive bar 504 is further translatable, independent of plunger 200 and drive housing 502, from the second position, to a third position, corresponding to the second approximated position of jaw members 410, 420 (FIG. 6B).

Drive housing 502 of drive assembly 500 may be formed at least partially from a thermally conductive material and defines a proximal end 507, a distal end 509, and an internal chamber 510. Proximal end 507 of drive housing 502 includes an engagement feature 516 configured complementary to engagement feature 216 of rod 210 of plunger 200 for engaging drive housing 502 and rod 210 to one another, e.g., via snap-fit engagement. However, rod 210 and drive housing 502 may alternatively be engaged to one another in any other suitable fashion, e.g., via adhesion, friction-fitting, welding, etc., or may be monolithically formed with one another as a single component. Distal end 509 of drive housing 502 defines an aperture 511 therethrough that is centered about longitudinal axis "X-X" and is configured to receive proximal end 505 of drive bar 504 therethrough.

Figure 5A:
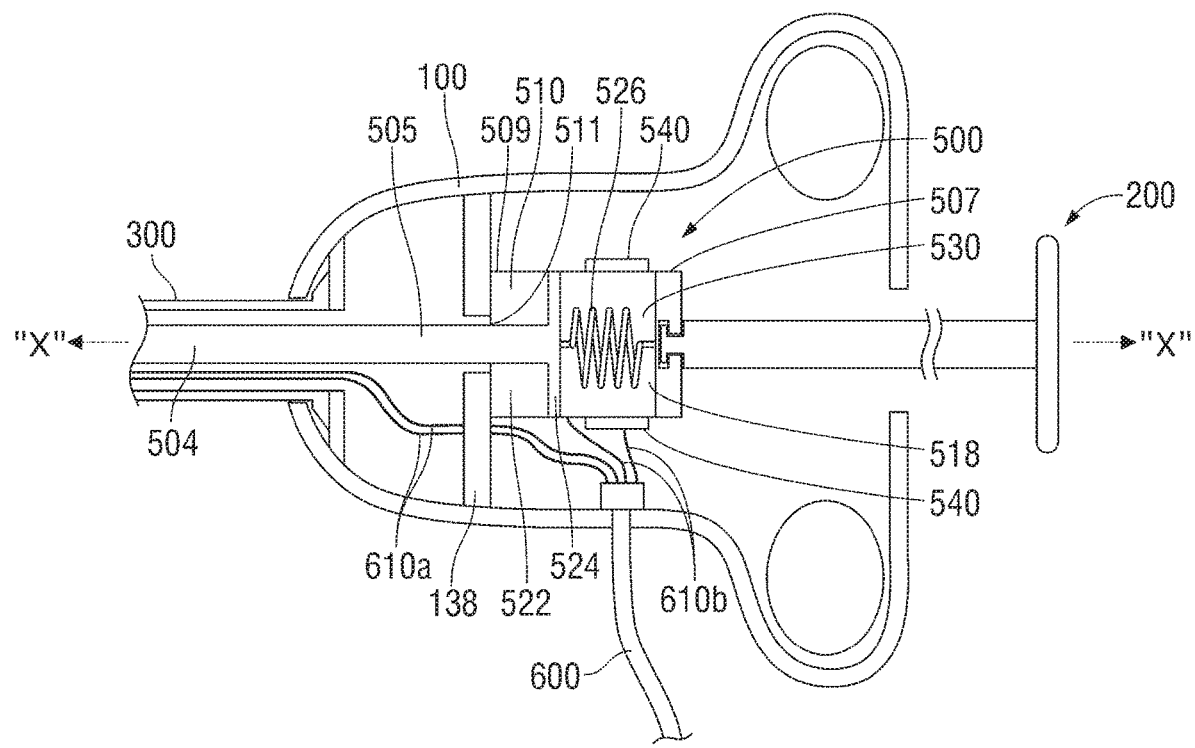
FIG. 5A is a side, cut-away view of the housing of the surgical instrument of FIG. 1 showing the internal components thereof, wherein the drive assembly of the surgical instrument is disposed in a second position.
Figure 6A:
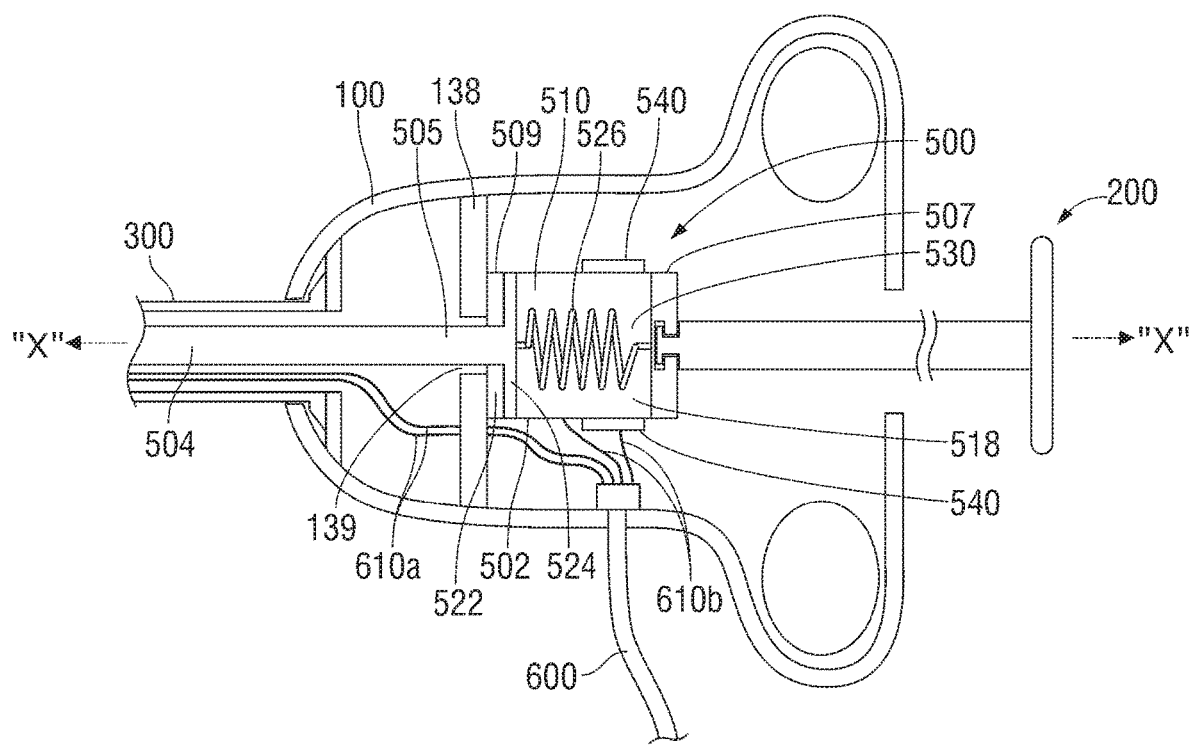
FIG. 6A is a side, cut-away view of the housing of the surgical instrument of FIG. 1 showing the internal components thereof, wherein the drive assembly of the surgical instrument is disposed in a third position.

Proximal end 505 of drive bar 504, as mentioned above, extends proximally through aperture 511 of drive housing 502 and into internal chamber 510 of drive housing 502 to divide internal chamber 510 into a proximal portion 518 and a distal portion 522. More specifically, drive bar 504 includes a proximal stop 524 disposed at proximal end 507 thereof that generally approximates the cross-sectional area of internal chamber 510 so as to function as a piston disposed within internal chamber 510. Proximal stop 524 is longitudinally translatable within and relative to internal chamber 510 of drive housing 502 to translate drive bar 504 relative to drive housing 502 between the second and third positions (FIGS. 5A and 6A, respectively). As can be appreciated, distal translation of proximal stop 524 within internal chamber 510 and relative to drive housing 502 increases the volume of proximal portion 518 while correspondingly decreasing the volume of distal portion 522 (and vice versa, e.g., proximal translation of proximal stop 524 within internal chamber 510 and relative to drive housing 502 decreases the volume of proximal portion 518 while correspondingly increasing the volume of distal portion 522). Proximal stop 524 may be formed at least partially from a resilient material, or may otherwise be configured, to establish a sealing relation with drive housing 502, such that proximal and distal portions 518, 522, respectively, of internal chamber 510 remain substantially sealed from one another.

With continued reference to FIG. 3, proximal portion 518 of drive housing 502 includes a biasing member, e.g., a spring 526, longitudinally positioned between proximal end 507 of drive housing 502 and proximal stop 524 of drive bar 504. Proximal portion 518 of drive housing 502 further includes a thermally-activatable material 530, e.g., a wax, oil, or any other suitable material having a thermally-dependent viscosity. Thermally-activatable material 530 is initially disposed in a solid (or more viscous) state that substantially fills the volume of proximal portion 518. Spring 526 is encased within the solid (or more viscous) thermally-activatable material 530 and is retained in a compressed, or loaded position. That is, although spring 526 is loaded, spring 526 is inhibited from biasing proximal stop 524 distally relative to drive housing 502 due to the encasement of spring 526 within the solid (or more viscous) thermally-activatable material 530. Rather, thermally-activatable material 530 retains spring 526 in its loaded position. Thermally-activatable material 530, in its solid (or more viscous) state, may further be configured to couple proximal end 507 of drive housing 502 and proximal stop 524 of drive bar 504 to one another to inhibit relative movement therebetween when material 530 is disposed in its solid (or more viscous) state. As such, material 530, in its solid (or more viscous) state, inhibits drive bar 504 from being translated relative to drive housing 502 from the second position (FIG. 5A) to the third position (FIG. 6A).

As shown in FIG. 3, drive housing 502 additionally includes a pair of heaters 540 (although greater or fewer than two heaters may also be provided) disposed on either side of proximal portion 518 of drive housing 502. Each heater 540 is coupled to a wire 610b that extends through cable 600 to couple heaters 540 to the generator (not shown) used for providing energy to jaw members 410, 420, or any other suitable energy source. Alternatively, heaters 540 may be self-powered, e.g., via a battery (not explicitly shown) disposed within or adjacent to heaters 540. Heaters 540 may include any suitable mechanism for selectively heating proximal portion 518 of drive housing 502, e.g., heaters 540 may include heating coils, transistors, resistive heaters, etc. Positioning heaters 540 on the exterior of drive housing 502 is sufficient to heat the thermally-activatable material 530 disposed within proximal portion 518 of drive housing 502 due to the formation of drive housing 502 from a thermally conductive material. However, in embodiments where drive housing 502 is formed from an insulative material, heaters 540 may be disposed within drive housing 502 to permit sufficient heating of material 530. Heaters 540, as will be described below, are configured to heat the thermally-activatable material 530 sufficiently so as to activate, or transition material 530 from the solid (or more viscous) state to a fluid (or less viscous) state, thereby permitting spring 526 to bias drive bar 504 distally to transition drive bar from the second position (FIG. 5A) to the third position (FIG. 6A).

Heaters 540 may be activated manually, e.g., upon translation of plunger 200 from the proximal position to the distal position, via activating one or more switch assemblies 132, 134 disposed on handle assembly 100, via activating one or more controls on the generator (not shown) or other energy source, or via any other suitable mechanism. Alternatively, heaters 540 may be automatically actuated, e.g., via one or more sensors (not explicitly shown) configured to sense the properties of jaw members 410, 420 and/or tissue disposed therebetween.

Referring again to FIGS. 1-3, end effector assembly 400, as mentioned above, includes first and second jaw members 410, 420, respectively, that are moveable relative to one another between a spaced-apart position (FIG. 4B), a first approximated position (FIG. 5B), and a second approximated position (FIG. 6B). Each jaw member 410, 420 includes an opposed, tissue contacting surface 412, 422, respectively. One or both of the jaw members, e.g., jaw member 410, includes a tissue contacting member 414 disposed on or along tissue contacting surface 412 that is configured to facilitate the transmission of light energy from the light energy source, e.g., the generator (not shown), to tissue grasped between jaw members 410, 420. More specifically, cable 600 and wires 610a (which extend distally through shaft 300) couple tissue contacting member 414 of jaw member 410 to the light energy source such that light energy may be transmitted between jaw members 410, 420, as indicated by arrows "A" (FIGS. 5B and 6B) and through tissue grasped therebetween (although energy may be transmitted between jaw members 410, 420 and through tissue in the opposite direction, in both directions, and/or in a transverse direction). The other jaw member, e.g., jaw member 420, may alternatively or additionally include a tissue contacting member 424 disposed on or along tissue contacting surface 422 that is configured to receive, absorb, or reflect the light energy transmitted from jaw member 410 and through tissue.

Figure 4A:
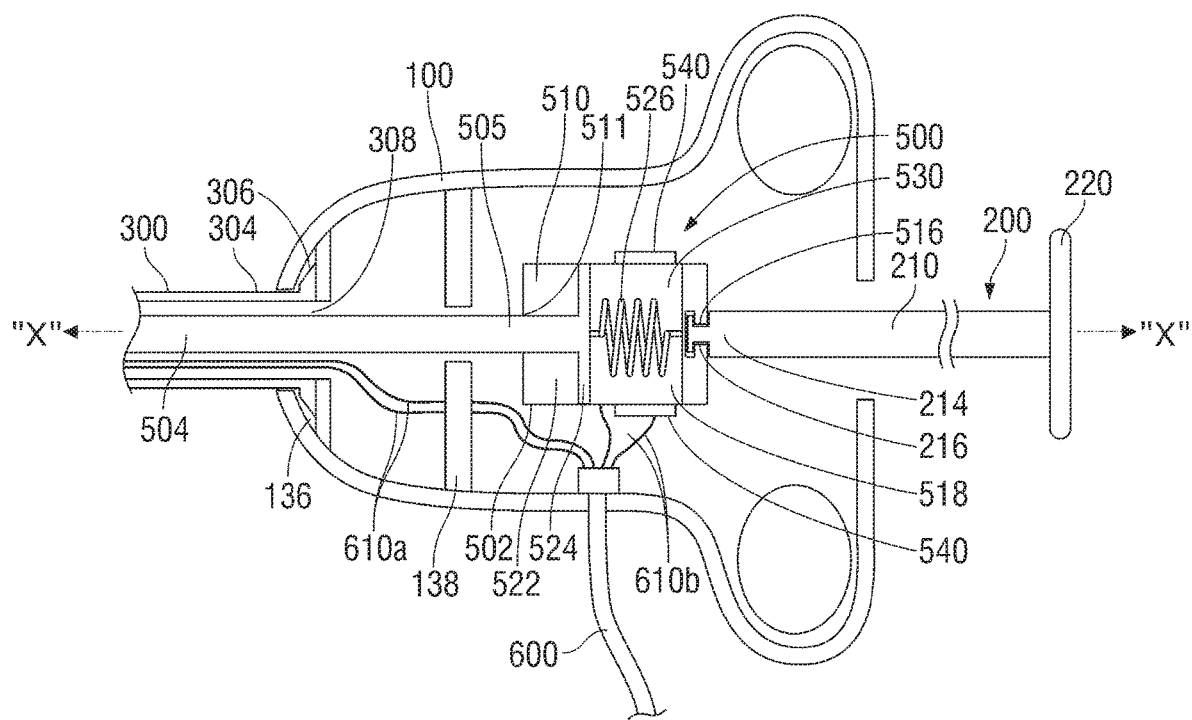
FIG. 4A is a side, cut-away view of the housing of the surgical instrument of FIG. 1 showing the internal components thereof, wherein the drive assembly of the surgical instrument is disposed in a first position.

Turning now to FIGS. 1, 2 and 4A-6B, the use and operation of forceps 10 is described. Initially, as shown in FIGS. 1 and 4A-4B, plunger 200 is disposed in the proximal position and drive bar 504 and drive housing 502 of drive assembly 500 are disposed in the first position. Accordingly, at this point, jaw members 410, 420 of end effector assembly 400 are disposed in the spaced-apart position. In this position, forceps 10 may be manipulated and/or maneuvered to position end effector assembly 400 such that tissue to be treated, e.g., sealed and/or cut, is disposed between jaw members 410, 420.

Figure 4B:
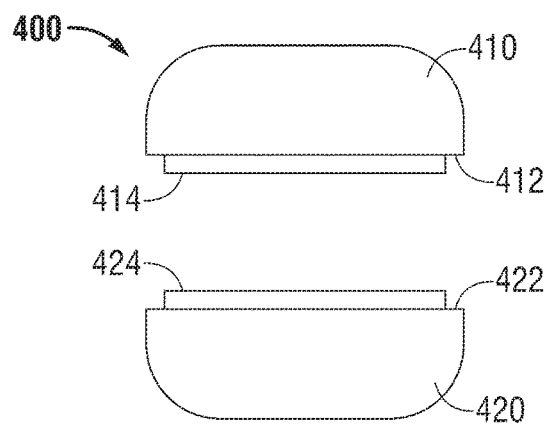
FIG. 4B is a transverse, cross-sectional view of the end effector assembly of the surgical instrument of FIG. 1 shown in the spaced-apart position.
Figure 5B:
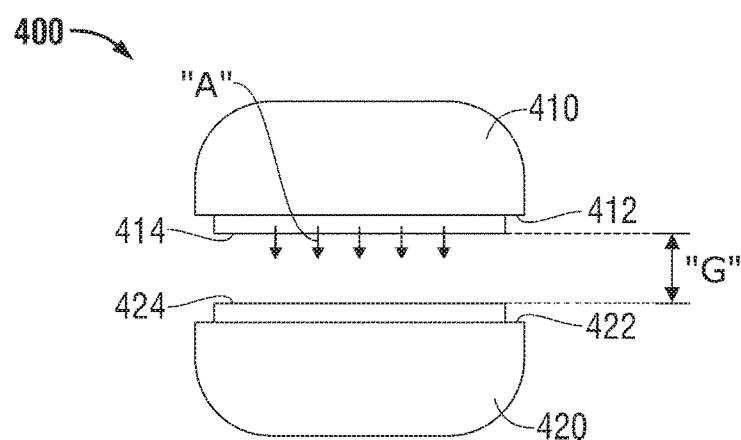
FIG. 5B is a transverse, cross-sectional view of the end effector assembly of the surgical instrument of FIG. 1 shown in a first approximated position.
Figure 6B:
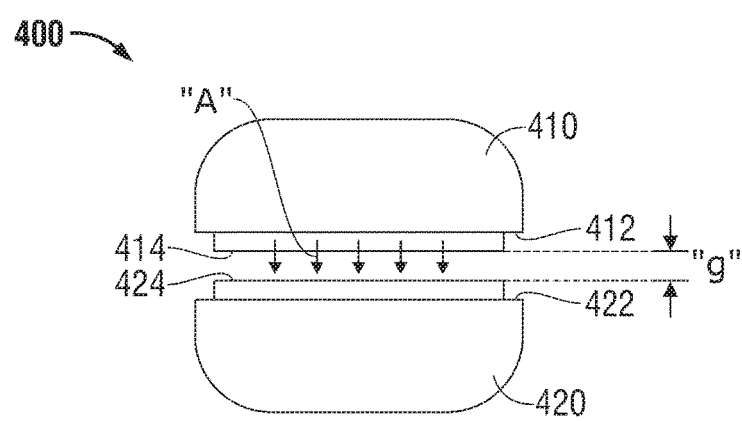
FIG. 6B is a transverse, cross-sectional view of the end effector assembly of the surgical instrument of FIG. 1 shown in a second approximated position.

Turning now to FIGS. 4A-4B in conjunction with FIGS. 5A-5B, with jaw members 410, 420 of end effector assembly 400 in position, the surgeon, while grasping both handle assembly 100 and plunger 200, translates knob 230 of plunger 200 distally relative to handle assembly 100, thereby translating plunger 200 from the proximal position to the distal position. Translation of plunger 200 from the proximal position to the distal position, in turn, effects cooperative translation of drive bar 504 and drive housing 502 from the first position to the second position, such that jaw members 410, 420 are pivoted relative to one another from the spaced-apart position to the first approximated position (FIG. 4B) to grasp tissue therebetween. A transversely-positioned wall 138 disposed within handle assembly 100 inhibits further distal translation of drive housing 502 beyond the second position and, thus, inhibits further distal translation of plunger 200 beyond the distal position. However, wall 138 includes an aperture 139 defined therethrough to permit passage of drive bar 504 distally beyond wall 138. In other words, wall 138 functions as a stop, thus defining the distal position of plunger 200, the second position of drive housing 502, and correspondingly, the first approximated position of jaw members 410, 420. In this first approximated position, tissue contacting members 414, 424 of jaw members 410, 420, respectively, define a gap distance "G" therebetween.

At this point, the material 530 disposed within proximal portion 518 of drive housing 502 remains in the solid state such that spring 526 remains encased therein in the loaded position. Further, as mentioned above, material 530, in its solid (or more viscous) state, retains drive bar 504 in fixed position relative to drive housing 502. As such, at this point, with material 530 in its solid (or more viscous) state, and with drive housing 502 disposed in the second position and inhibited by wall 138 from translating further distally, drive bar 504 is likewise inhibited from being translated beyond the second position (FIG. 5A).

With jaw members 410, 420 disposed in the first approximated position defining gap distance "G" therebetween, as shown in FIG. 5B, a relatively smaller pressure is applied to tissue grasped therebetween. That is, with a relatively larger gap distance "G" between jaw members 410, 420, the pressure exerted on tissue grasped therebetween is relatively smaller. As will be described below, upon translation of drive bar 504 from the second position to the third position, jaw members 410, 420 are permitted to further approximate relative to one another to the second approximated position (FIG. 6B), wherein a smaller gap distance "g" is defined between jaw members 410, 420 and, thus, a greater pressure is applied to tissue grasped between jaw members 410, 420.

Referring to FIGS. 5A-5B, with jaw members 410, 420 disposed in the first approximated position and grasping tissue between tissue contacting members 414, 424, respectively, thereof, energy may be transmitted from tissue contacting member 414 of jaw member 410, through tissue, to tissue contacting member 424 of jaw member 420, as indicated by arrows "A" (although energy may alternatively be transmitted between one or both of tissue contacting members 414, 424 in either or both directions). Activation of the energy may be effected via actuating one or more of first and second switch assemblies 132 and 134 (FIG. 1). At this point, with jaw members 410, 420 disposed in the first approximated position defining first gap distance "G" therebetween, a relatively smaller pressure is applied to tissue, and, thus, the absorption of light energy by tissue is maximized at this beginning stage of tissue treatment.

With reference also to FIGS. 6A-6B, once tissue has absorbed a sufficient amount of energy, upon satisfaction of a pre-determined condition, time, and/or function, upon other suitable automatic activation, or upon manual activation, e.g., via actuation of one or more of switch assemblies 132, 134 (FIG. 1), heaters 540 are activated. Upon activation of heaters 540, as mentioned above, proximal portion 518 of drive housing 502 is heated such that material 530 begins to melt (or become less viscous) from its solid (more viscous) state to a more fluid (less viscous) state. As material 530 melts, the loaded spring 526 is no longer fixed in encasement within the material 530, but is permitted to elongate under bias back towards its at-rest state. As spring 526 is elongated back towards its at-rest position, the distal end of spring 526 eventually contacts proximal stop 524 and, upon further elongation of spring 526, proximal stop 524 is urged distally towards distal end 509 of drive housing 502. More specifically, as proximal stop 524 is urged distally, drive bar 504 is likewise urged distally independent of drive housing 502 from the second position towards the third position, as progressively shown from FIG. 5A to FIG. 6A, such that proximal stop 524 is moved to distal end 509 of drive housing 502 and such that jaw members 410, 420 are moved to the second approximated position defining gap distance "g" therebetween. Since jaw members 410, 420 are approximated further about tissue, a greater pressure is applied to tissue grasped between jaw members 410, 420.

As can be appreciated, at the beginning of the melting of material 530, e.g., where material 530 is still substantially solid, material 530 is relatively more viscous, thus dampening, or slowing the return of spring 526 back towards its at-rest position. As material 530 is melted further, e.g., as material 530 becomes more fluid, material 530 is less viscous and, as a result, spring 526 is permitted to elongated further and at an increased rate. Accordingly, heaters 540 may be controlled to heat and, ultimately, melt material 530 at a pre-determined rate, according to a predetermined function, or in any other suitable fashion so as to control the translation of drive bar 504 from the second position to the third position, thus controlling the movement of jaw members 410, 420 from the first approximated position to the second approximated position. Alternatively, the wax, oil, or other material used to form thermally-activatable material 530 may be configured to likewise achieve a desired rate of movement of jaw member 410, 420 as the material 530 is transitioned from its more viscous state to its less viscous state.

With jaw members 410, 420 disposed in the second approximated position, as shown in FIG. 6B, second gap distance "g," which is smaller than first gap distance "G," is defined between tissue contacting members 414, 424 of jaw members 410, 420, respectively, and, as a result, a relatively larger pressure is applied to tissue grasped therebetween. With jaw members 410, 420 disposed in this second approximated position applying an increased pressure to tissue, the transmission of energy from tissue contacting member 414 of jaw member 410, through tissue, to tissue contacting member 424 of jaw member 420 may be continued to complete formation of a tissue seal and/or to divide tissue along the previously formed tissue seal. Alternatively, jaw members 410, 420 may be moved to an intermediate approximated position for completion of the tissue seal, and may then be moved to the second approximated position for cutting tissue along the previously formed tissue seal. Further, heaters 540 may be activated automatically upon supplying energy to jaw members 410, 420 such that jaw members 410, 420 are continuously moved from the first approximated position to the second approximated position to seal tissue, seal and cut tissue, or otherwise treat tissue.

At the completion of tissue treatment, e.g., sealing and/or cutting of tissue, jaw members 410, 420 are returned to the spaced-apart position, e.g., via translating plunger 200 proximally back to the proximal position, and end effector assembly 200 is removed from the surgical site (or is repositioned adjacent other tissue to be treated).

Figure 7A:
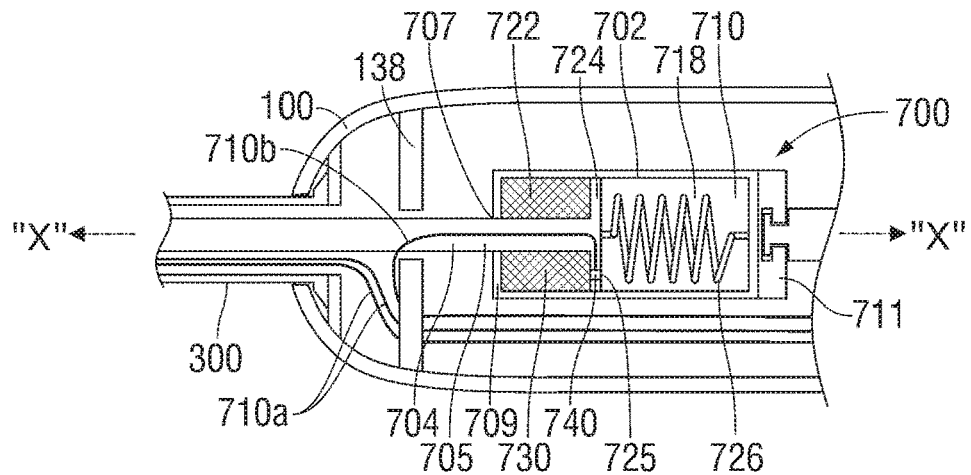
FIG. 7A is a side, cut-away view of the housing of another embodiment of a surgical instrument provided in accordance with the present disclosure, wherein the drive assembly of the surgical instrument is disposed in a first position.
Figure 7B:
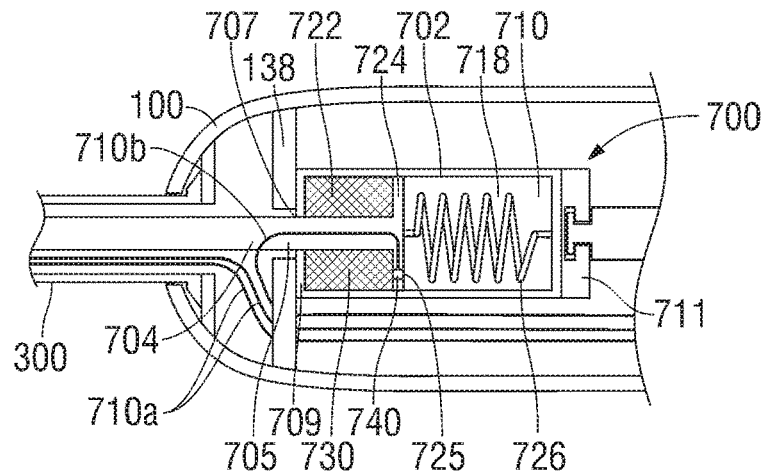
FIG. 7B is a side, cut-away view of the housing of the surgical instrument of FIG. 7A, wherein the drive assembly of the surgical instrument is disposed in a second position.
Figure 7C:
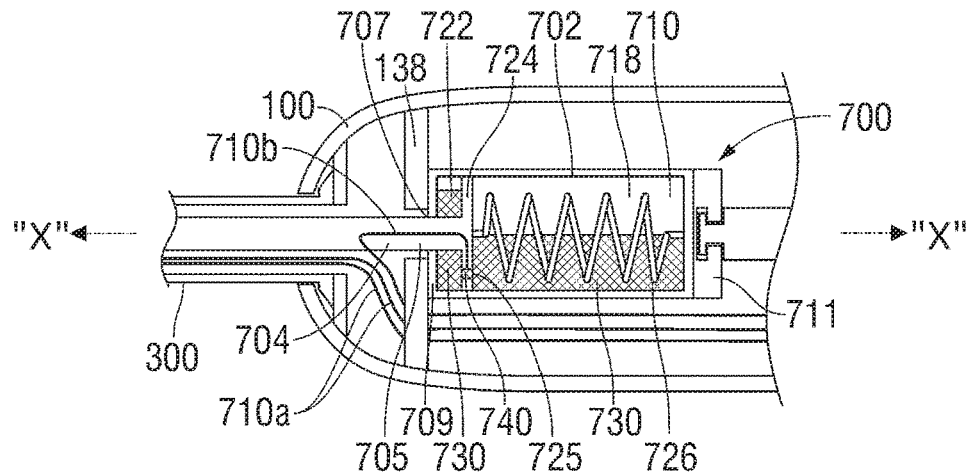
FIG. 7C is a side, cut-away view of the housing of the surgical instrument of FIG. 7A, wherein the drive assembly of the surgical instrument is disposed in a third position.

Turning now to FIGS. 7A-7C, in conjunction with FIGS. 1-2, another embodiment of a drive assembly configured for use with forceps 10, or any other suitable surgical instrument, is shown generally identified by reference numeral 700. Drive assembly 700 is similar to drive assembly 500 (FIGS. 3, 4A, 5A and 6A) and is likewise configured for use with forceps 10 and end effector assembly 400 (although drive assembly 700 may alternatively be configured for use with forceps 10' (FIGS. 8A-8B) or any other suitable surgical instrument and/or end effector assembly). Thus, only the differences between drive assembly 700 and drive assembly 500 (FIGS. 3, 4A, 5A and 6A) will be described in detail hereinbelow, while the similarities will be summarized or omitted entirely.

Drive assembly 700 generally includes a drive housing 702 and a drive bar 704 coupled to and extending distally from drive housing 702. Drive bar 704 extends distally from drive housing 702, though shaft 300, ultimately engaging jaw members 410, 420. As such, longitudinal translation of drive bar 704 relative to end effector assembly 400 pivots jaw members 410, 420 relative to one another between the spaced-apart position (FIG. 4B), the first approximated position (FIG. 5B), and the second approximated position (FIG. 6B). Similar to drive bar 504 of drive assembly 500 (FIGS. 3, 4A, 5A and 6A), drive bar 704 is longitudinally translatable, in conjunction with drive housing 702, between a first position (FIG. 7A), corresponding to the spaced-apart position of jaw members 410, 420 (FIG. 4B), and a second position (FIG. 7B), corresponding to the first approximated position of jaw members 410, 420 (FIG. 5B). Drive bar 704 is further translatable, independent of drive housing 702, from the second position (FIG. 7B), to a third position (FIG. 7C), corresponding to the second approximated position of jaw members 410, 420 (FIG. 6B).

Proximal end 705 of drive bar 704 extends proximally through aperture 707 of drive housing 702 and into internal chamber 710 of drive housing 702 to divide internal chamber 710 into a proximal portion 718 and a distal portion 722. More specifically, drive bar 704 includes a proximal stop 724 disposed at proximal end 705 thereof that is longitudinally translatable within and relative to internal chamber 710 of drive housing 702 to translate drive bar 704 relative to drive housing 702 between the second and third positions (FIGS. 7B and 7C, respectively). Proximal stop 724 establishes a sealing relation with drive housing 702 such that proximal and distal portions 718, 722, respectively, of internal chamber 710 remain substantially sealed from one another. Proximal stop 724 further includes a valve 740 disposed within an aperture 725 extending longitudinally therethrough that, as will be described in greater detail below, selectively permits fluid 730 to flow between the proximal and distal portions 718, 722, respectively, of drive housing 702. Valve 740 may be manually mechanically or electrically actuated via one or more wires 710b coupling valve 740 to a control, e.g., one or more of switch assembly 132, 134 (FIGS. 1-2), and/or an energy source, e.g., a generator (not shown), or may be automatically activated.

With continued reference to FIGS. 7A-7C, in conjunction with FIGS. 1-2, proximal portion 718 of drive housing 702 includes a biasing member, e.g., a spring 726, longitudinally positioned between proximal end 709 of drive housing 702 and proximal stop 724 of drive bar 704. Spring 726 is initially disposed in a compressed, or loaded condition, as shown in FIG. 7A. Distal portion 722 of drive housing 702, initially, is substantially filed with a fluid 730, e.g., air or any other suitable gas; water, saline, oil, or any other suitable liquid; or any suitable liquid-gas mixture. Further, valve 740 of proximal stop 724 is initially disposed in a closed condition so as to inhibit the passage of fluid 730 from distal portion 722 of drive housing 702 to proximal portion 718 of drive housing 702 (and vice versa). That is, with proximal portion 718 substantially filled with fluid 730 and with valve 740 closed, spring 726 is retained in the loaded condition since, due to the substantial filling of proximal portion 718 of drive housing 702 with fluid 730, proximal stop 724 is inhibited from being translated further distally under the bias of spring 726. Rather, spring 726 is retained in its loaded position.

With reference to FIGS. 7A-7C, in conjunction with FIGS. 4B, 5B and 6B, respectively, the use and operation of drive assembly 700 is described. Initially, drive assembly 700 is disposed in the first position, as shown in FIG. 7A and, correspondingly, jaw members 410, 420 of end effector assembly 400 are disposed in the spaced-apart position, as shown in FIG. 4B. In this position, forceps 10 may be manipulated and/or maneuvered to position end effector assembly 400 such that tissue to be treated, e.g., sealed and/or cut, is disposed between jaw members 410, 420.

Upon translation of drive assembly 700 to the second position, e.g., upon translation of plunger 200 from the proximal position to the distal position, drive bar 704 and drive housing 702 are cooperatively translated from the first position to the second position, such that jaw members 410, 420 are pivoted relative to one another from the spaced-apart position (FIG. 4B) to the first approximated position (FIG. 5B) to grasp tissue therebetween. More specifically, drive bar 704 and drive housing 702 are moved in cooperation with one another since, at this point, valve 740 remains closed, thus inhibiting spring 726 from elongating and urging proximal stop 724 and drive bar 704 distally relative to drive housing 702.

With jaw members 410, 420 disposed in the first approximated position defining gap distance "G" therebetween, as shown in FIG. 5B, a relatively smaller pressure is applied to tissue grasped therebetween. In this position, with jaw members 410, 420 grasping tissue between tissue contacting members 414, 424, respectively, thereof, energy may be transmitted from the energy source (not shown) to tissue contacting member 414 of jaw member 410, e.g., via wires 710a, through tissue, to tissue contacting member 424 of jaw member 420, as indicated by arrows "A" (although energy may alternatively be transmitted between one or both of tissue contacting members 414, 424 in either or both directions) such that, due to the relatively small pressure being applied to tissue, maximum absorption of light energy by tissue at the beginning of tissue treatment is facilitated.

Once tissue has absorbed a sufficient amount of energy, upon satisfaction of a pre-determined condition, time, and/or function, upon other suitable automatic activation, or upon manual activation, e.g., via actuation of one or more of switch assemblies 132, 134 (FIG. 1), valve 740 may be opened. When valve 740 is opened, fluid 730 is permitted to flow through proximal stop 724 from proximal portion 718 of drive housing to distal portion 722 thereof, ultimately allowing spring 726 to elongate back towards its at-rest position, thereby urging proximal stop 724 distally towards distal end 711 of drive housing 702. As proximal stop 724 is urged distally, drive bar 704 is likewise urged distally, independent of drive housing 702, from the second position towards the third position, as shown progressively from FIG. 7B to FIG. 7C, wherein proximal stop 724 is disposed at distal end 711 of drive housing 702 and wherein jaw members 410, 420 are moved to the second approximated position defining gap distance "g" therebetween (see FIG. 6B). With jaw members 410, 420 approximated to this second approximated position defining a smaller gap distance "g" therebetween, a greater pressure is applied to tissue grasped between jaw members 410, 420. As can be appreciated, valve 740 may be opened to various different positions, thus allowing a greater or lesser amount of fluid 730 to pass therethrough in order to control the rate at which the pressure applied to tissue is increased, e.g., the rate at which drive bar 704 is translated between the second and third positions. Further, valve 740 may be selectively controlled, e.g., incrementally opened and closed, to define various incremental steps for incrementally increasing the pressure applied to tissue grasped between jaw members 410, 420. The viscosity of the fluid 730 chosen also effects the rate that fluid 730 flows between proximal and distal portions 718, 722, respectively, of drive housing 702 and, thus, may be selected in accordance with a desired rate of approximation of jaw members 410, 420 from the first approximated position (FIG. 5B) to the second approximated position (FIG. 6B).

With jaw members 410, 420 disposed in the second approximated position, as shown in FIG. 6B, second gap distance "g," which is smaller than first gap distance "G," is defined between tissue contacting members 414, 424 of jaw members 410, 420, respectively, and, as a result, a relatively larger pressure is applied to tissue grasped therebetween. With jaw members 410, 420 disposed in this second approximated position applying an increased pressure to tissue, the transmission of energy from tissue contacting member 414 of jaw member 410, through tissue, to tissue contacting member 424 of jaw member 420 may be continued to complete formation of a tissue seal and/or to divide tissue along the previously formed tissue seal. Thereafter, plunger 200 may be retracted back to the proximal position to open jaw members 410, 420 and release the previously treated tissue grasped therebetween such that jaw members 410, 420 may be removed from the surgical site (or repositioned adjacent other tissue to be treated).

Figure 8A:
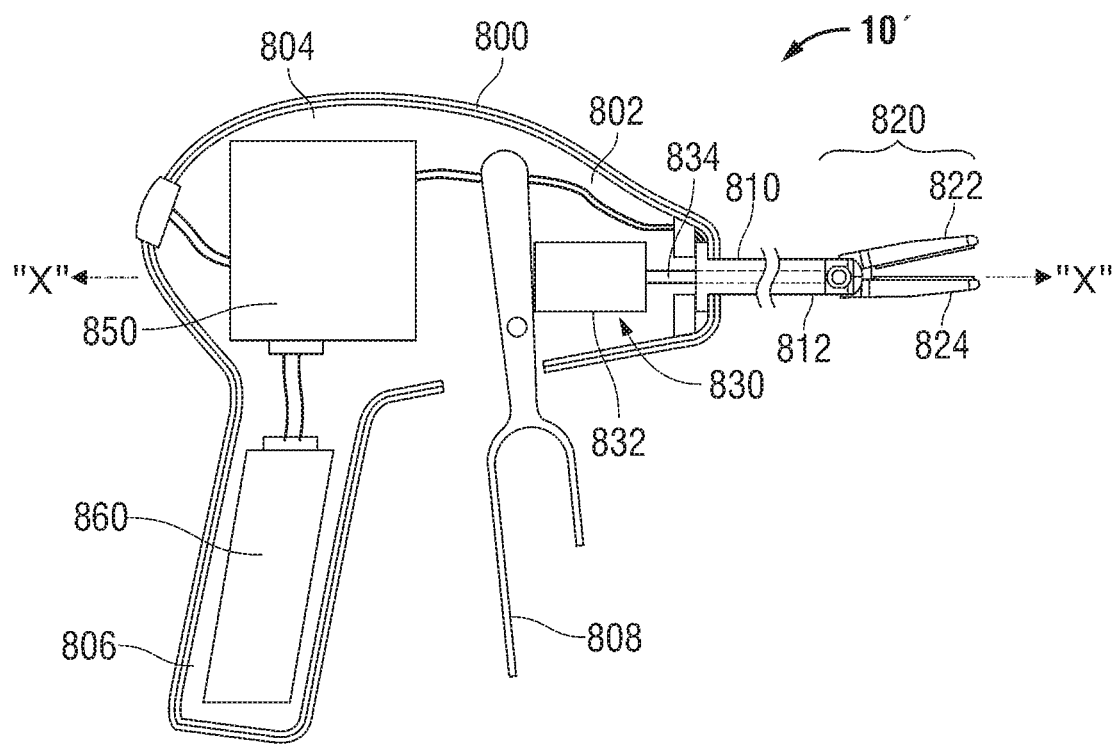
FIG. 8A is a side view of another embodiment of a surgical instrument provided in accordance with the present disclosure shown, wherein a portion of the housing has been removed to show the internal components thereof and wherein the end effector assembly of the surgical instrument is disposed in a spaced-apart position.
Figure 8B:
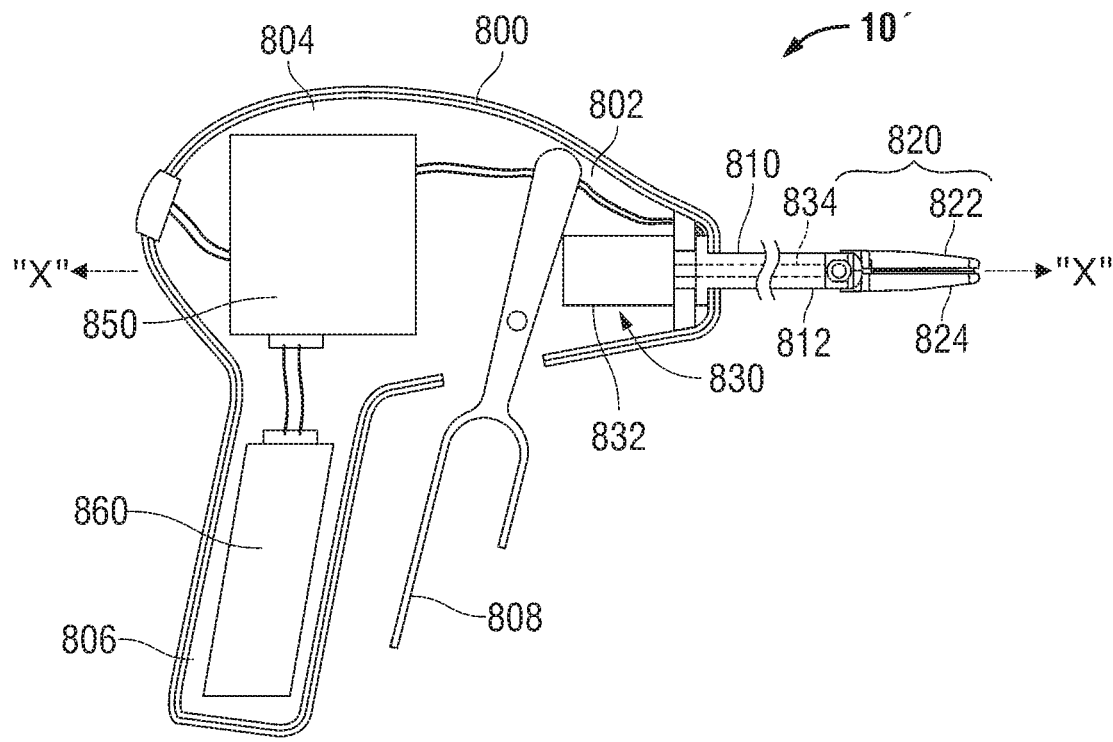
FIG. 8B is a side view of the surgical instrument of FIG. 8A, wherein a portion of the housing has been removed to show the internal components thereof and wherein the end effector assembly of the surgical instrument is disposed in an approximated position.

Turning now to FIGS. 8A-8B, another embodiment of a forceps 10' is shown generally including a housing 800, an elongated shaft 810, an end effector assembly 820 disposed at distal end 812 of shaft 810, and a drive assembly 830 disposed within housing 800 and operably coupled to end effector assembly 820 for controlling operation of end effector assembly 820. End effector assembly 820 may be similar to end effector assembly 400, described above (see FIGS. 3, 4B, 5B and 6B), or may be any other suitable end effector assembly. Housing 800 houses drive assembly 830 therein, which may be configured similarly to either of drive assemblies 500 and 700, discussed above (see FIGS. 3, 4A, 5A, 6A and FIGS. 7A-7C, respectively). More specifically, drive assembly 830 is housed within distal portion 802 of housing 800. Housing 800 further includes a generally hollow proximal portion 704 that is configured to receive a portable generator 850 therein, and a generally hollow fixed handle portion 806 that is configured to receive a battery 860 therein. Generator 850 and battery 860 are coupled to one another, to drive assembly 830, and to end effector assembly 820 for controlling the supply of energy to jaw members 822, 824 of end effector assembly 820 and/or drive assembly 830 to facilitate treating tissue. As can be appreciated, the relatively compact configuration of drive assembly 830 (which is similar to drive assembly 500 or drive assembly 700 (FIGS. 3, 4A, 5A, 6A and FIGS. 7A-7C, respectively)), permit positioning of the drive assembly 830 in distal portion 802 of housing 800 while leaving sufficient space for generator 850 and battery 806 to also be positioned within housing 800. Thus, forceps 10' provides a relatively compact, portable surgical instrument (e.g., a surgical instrument incorporating a generator and battery into the housing thereof) having a drive assembly 830 that facilitates movement of jaw members 822, 824 between a spaced-apart position and first and second approximated positions for energy-based tissue treatment.

In use, forceps 10' functions similar to forceps 10 (FIGS. 1-3), described above. However, rather than providing a plunger 200 (FIGS. 1-3), forceps 10' includes a movable handle 808 movable between an initial position (FIG. 8A) and an actuated position (FIG. 8B) for moving drive assembly 830 from a first position to a second position and, correspondingly moving jaw members 822, 824 from the spaced-apart position (FIG. 8A) and the first approximated position (FIG. 8B). Thereafter, drive assembly 830 is further operable, as described above with respect to drive assemblies 500, 700 (FIGS. 3, 4A, 5A, 6A and FIGS. 7A-7C, respectively), to translate drive bar 834, independent of drive housing 832, from the second position to a third position corresponding to the second approximated position of jaw members 822, 824. Any or all of the features of forceps 10 (FIGS. 1-3) and/or drive assemblies 500, 700 (FIGS. 3, 4A, 5A, 6A and FIGS. 7A-7C, respectively) described above may also be incorporated into forceps 10'.

Figure 9A:
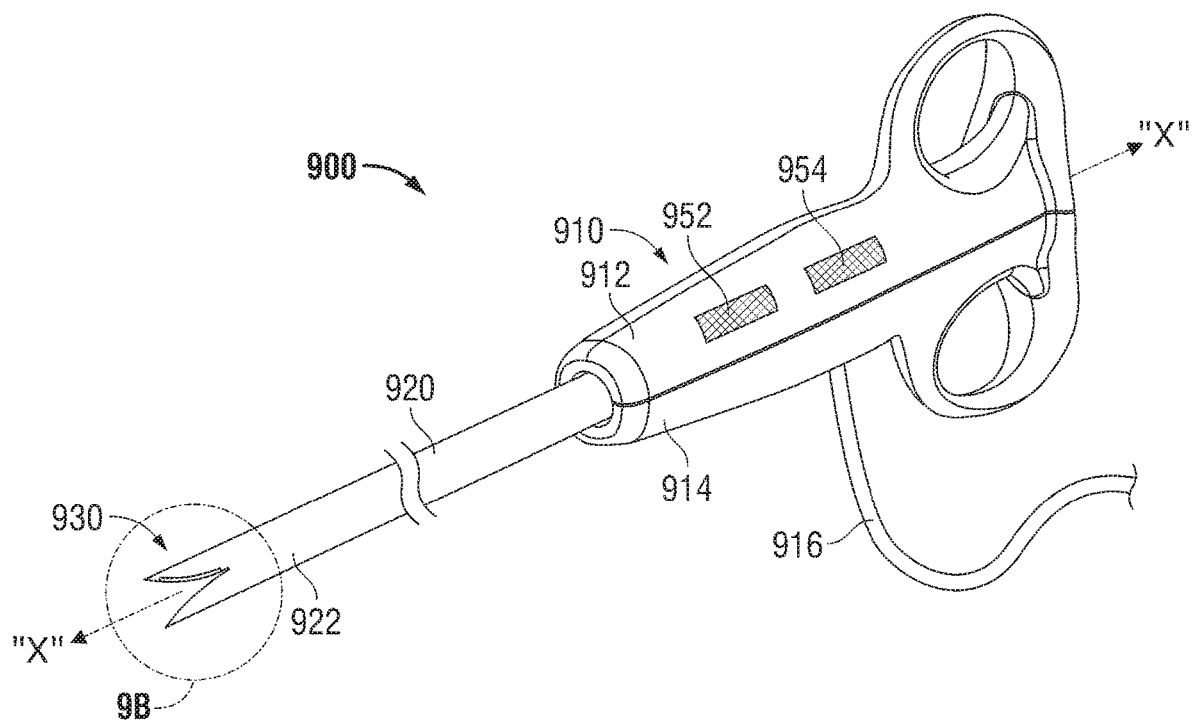
FIG. 9A is a front, perspective view of another embodiment of a surgical instrument provided in accordance with the present disclosure.
Figure 9B:
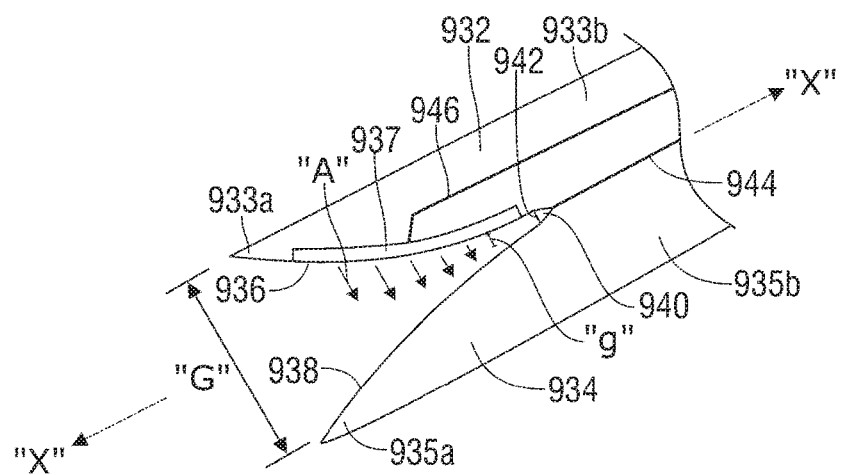
FIG. 9B is an enlarged, perspective, cut-away view of the area of detail indicated in FIG. 9A.

Turning now to FIGS. 9A-9B, another embodiment of a forceps provided in accordance with the present disclosure is shown generally identified by reference numeral 900. Forceps 900 includes a housing 910, a shaft 920 extending distally form housing 910, and an end effector assembly 930 disposed at distal end 922 of shaft 920. Housing 910 is formed from cooperating housing parts 912, 914 (although other configurations are contemplated) and includes a cable 916 extending therefrom that ultimately connects to an energy source (not shown) for providing energy to end effector assembly 930. Alternatively, housing 910 may be configured to retain a portable energy source (not shown) therein. Housing 910 is particularly suitable for retaining a portable energy source therein in that housing 910 does not include any of the drive assembly or movable handle components typically associated with the housing of a forceps. Alternatively, housing 910 may simply configured as a small, lightweight instrument configured to connect to an external energy source, e.g., via cable 916. Both of these configurations are facilitated because, as will be described in greater detail below, the components of forceps 900 are static, i.e., forceps 900 does not require moving components.

With continued reference to FIGS. 9A-9B, shaft 920 includes a bifurcated distal end 922 defining the first and second jaw members 932, 934, respectively, of end effector assembly 930. Each jaw member 932, 934 defines a diverging opposed surface 936, 938. More specifically, diverging opposed surfaces 936, 938 of jaw members 932, 934, respectively, extend outwardly and distally from heel 940 of end effector assembly 930 to distal ends 933a, 935a of jaw members 932, 934, respectively, such that jaw members 932, 934 define a first gap distance "G" therebetween at distal ends 933a, 935a, respectively, thereof, and a second, smaller gap distance "g" therebetween at proximal ends 933b, 935b, respectively, thereof. Heel 940 of end effector assembly 930 may define a cutting blade 942 that, as will be described in greater detail below, is configured to cut tissue disposed between jaw members 932, 934. Cutting blade 942 may also be coupled to the energy source (not shown), e.g., via wire 944, to facilitate energy-based cutting of tissue. One or both of the jaw members, e.g., jaw member 932, may further include a tissue contacting member 937 coupled to the source of energy, e.g., via wire 936, such that light energy may be transmitted between jaw members 932, 934, as indicated by arrows "A," and through tissue disposed therebetween (although energy may be transmitted between jaw members 932, 934 and through tissue in the opposite direction or in both directions).

Continuing with reference to FIGS. 9A-9B, the use and operation of forceps 900 is described. Initially, forceps 900 is positioned such that jaw members 932, 934 are positioned proximally of tissue to be treated. In instances where the tissue to be treated is underlying other tissue, forceps 900 may be advanced distally to dissect through the overlying tissue, e.g., such that the overlying tissue is passed between jaw members 932, 934 and, due to the configuration of jaw members 932, 934, is directed into contact with cutting blade 942 of heel 940 of end effector assembly 930 to dissect the tissue.

Once jaw members 932, 934 of end effector assembly 930 of forceps 900 are positioned proximally adjacent the tissue to be treated, energy may be supplied to jaw member 932, e.g., via activating one or more of switch assemblies 952, 954, such that light energy is transmitted between jaw members 932, 934 in the direction of arrows "A." Next, end effector assembly 930 may be advanced distally towards and, eventually, about tissue such that tissue enters the gap between jaw members 932, 934 and is moved proximally therethrough. Initially, when tissue is disposed towards distal tips ends 933a, 935a of jaw members 932, 934, respectively, a relatively small pressure is applied to tissue between jaw members 932, 934, due to the relatively larger gap distance "G" between jaw members 932, 934. Thus, at the beginning of the tissue treatment process, absorption of light energy by tissue is maximized.

As end effector assembly 930 is advanced further distally relative to tissue, the pressure applied to tissue is increased due to the fact that tissue is moved proximally between jaw members 932, 934 towards proximal ends 933b, 935b, respectively, thereof, wherein the gap distance "g" between jaw members 932, 934 is relatively small. Accordingly, as tissue is moved proximally relative to and between jaw members 932, 934, the pressure applied to tissue disposed therebetween is increased. As mentioned above, increasing the pressure after sufficient energy absorption has been achieved facilitates completion of the tissue seal.

Upon further advancement of end effector assembly 930 relative to tissue, tissue contacts cutting blade 942 of heel 940 of end effector assembly 930, which divides the tissue along the previously-formed tissue seal. As mentioned above, cutting blade 942 may be energized to facilitate cutting of tissue. Thereafter, end effector assembly 930 may be repositioned adjacent other tissue to be treated, and the above-described process can be repeated to treat, e.g., seal and/or cut, additional tissue.

Although the above is described in terms of three steps, it is envisioned that end effector assembly 930 be advanced continuously through tissue such that the application of energy under the first, relatively small pressure during the initial phase of tissue treatment; the application of energy under the second, increased pressure to complete formation of the tissue seal; and the cutting of tissue along the previously-formed tissue seal are segments of a continuous process, rather than incremental, discrete steps. As such, the surgeon may advance end effector assembly 930 through tissue to rapidly treat, e.g., seal and cut, one or more portions of tissue in a single, continuous motion.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
an end effector assembly including first and second jaw members movable relative to one another between a spaced-apart position, a first approximated position, and a second approximated position; and
a drive assembly including a drive housing and a drive bar having proximal and distal ends, the proximal end of the drive bar coupled to the drive housing, the distal end of the drive bar coupled to at least one of the jaw members;
wherein the drive housing defines an internal chamber having a fluid disposed therein, wherein the drive housing and the drive bar are selectively movable in conjunction with one another between a first location and a second location to move the jaw members between the spaced-apart position and the first approximated position, and wherein the drive assembly is selectively activatable to move the drive bar independent of the drive housing from the second location to a third location to move the jaw members from the first approximated position to the second approximated position,
wherein the drive bar includes a proximal stop disposed at the proximal end thereof, the proximal stop disposed within the internal chamber of the drive housing and movable within the internal chamber upon activation of the drive assembly to move the drive bar from the second location to the third location,
wherein the drive housing further includes a spring disposed within the internal chamber of the drive housing, the spring configured, upon activation of the drive assembly, to bias the drive bar distally relative to the drive housing to thereby move the drive bar from the second location to the third location,
wherein the proximal stop divides the internal chamber into a proximal portion and a distal portion and includes a valve that is transitionable between a closed condition, inhibiting passage of fluid through the valve from the distal portion to the proximal portion, and an open condition, permitting passage of fluid through the valve from the distal portion to the proximal portion,
wherein the valve is initially disposed in the closed condition such that the fluid substantially fills the proximal portion of the internal chamber, thus inhibiting movement of the drive bar from the second location to the third location.

2. The forceps according to claim 1, wherein, upon activation of the drive assembly, the valve is transitioned to the open condition to permit fluid to flow therethrough to thereby permit movement of the drive bar from the second location to the third location under the bias of the spring.

3. A forceps, comprising:
an end effector assembly including first and second jaw members movable relative to one another between a spaced-apart position, a first approximated, and a second approximated position;
a drive assembly, including:
a drive housing defining an internal chamber;
a drive bar coupled to the end effector assembly at a distal end thereof, a proximal end of the drive bar defining a proximal stop slidably disposed within the internal chamber of the drive housing, the drive bar and drive housing movable in conjunction with one another between a first location and a second location for moving the jaw members between the spaced-apart position and the first approximated position;
a spring disposed within the internal chamber of the drive housing, the spring configured to bias the drive bar distally relative to the drive housing;
a fluid substantially filling a proximal portion of the internal chamber defined between a distal end of the internal chamber and the proximal stop so as to inhibit the spring from biasing the drive bar distally relative to the drive housing; and
a valve disposed within an aperture extending through the proximal stop, the valve transitionable between a closed condition inhibiting the spring from biasing the drive bar distally relative to the drive housing, and an open condition permitting fluid to pass through the valve from the proximal portion of the internal chamber to a distal portion of the internal chamber defined between the proximal stop and a proximal end of the internal chamber, to thereby permit the spring to bias the drive bar distally relative to the drive housing from the second location to a third location to move the jaw members from the first approximated position to the second approximated position.

4. The forceps according to claim 3, wherein at least one of the jaw members is adapted to connect to a source of energy for treating tissue disposed between the jaw members.

5. The forceps according to claim 3, wherein the valve is configured to transition between the closed condition and the open condition according to a first pre-determined function such that the jaw members are moved between the first approximated position and the second approximated position in accordance with the first pre-determined function.

6. The forceps according to claim 3, wherein the fluid is configured to flow through the valve according to a second pre-determined function such that the jaw members are moved between the first approximated position and the second approximated position in accordance with the second pre-determined function.

\* \* \* \* \*